United States Patent

Himmler

(10) Patent No.: US 6,720,428 B2
(45) Date of Patent: Apr. 13, 2004

(54) METHOD FOR PRODUCING 2-(1,2,4-TRIAZOL-1-YL)-ETHANOLS

(75) Inventor: Thomas Himmler, Odenthal (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/203,148
(22) PCT Filed: Jan. 29, 2001
(86) PCT No.: PCT/EP01/00908
  § 371 (c)(1),
  (2), (4) Date: Aug. 6, 2002
(87) PCT Pub. No.: WO01/58884
  PCT Pub. Date: Aug. 16, 2001

(65) Prior Publication Data
  US 2003/0018201 A1 Jan. 23, 2003

(30) Foreign Application Priority Data
  Feb. 9, 2000 (DE) .......................................... 100 05 572

(51) Int. Cl.$^7$ ............................................. C07D 249/08
(52) U.S. Cl. ..................... 548/267.8; 564/310; 564/314
(58) Field of Search ...................... 548/267.8; 564/310, 564/314

(56) References Cited

U.S. PATENT DOCUMENTS 5,276,008 A * 1/1994 Kuhnt et al. ................. 504/273

FOREIGN PATENT DOCUMENTS

DE  40 30 039   3/1992
EP  0 502 307   9/1992

OTHER PUBLICATIONS

Tetrahedron Letters, vol. 30, No. 30, (month unavailable) 1989, pp. 4013–4016, "A General Anionic Mechanism for Thermodynamic Control of Regioselectivity in N-Alkylation and Acylation of Heterocycles", T. William Bentley, Ray V.H. Jones and Peter J. Wareham.
Angew. Chem. 72, (month unavailable) 1960, pp. 956–959, "Die Reaktion von Cyanurchlorid mit Dimethylformamid", H. Gold, E.H.U. Haberland.
Ber. Dtsch Chem. Ges. 16, (month unavailable) 1883, pp. 308–311, "Ueber die Verbindungen der Blausäure mit Chlor– und Bromwasserstoff", L. Claisen und F. Matthews.
Chem. Ber. 35, (month unavailable) 1902, pp. 2496–2511, "Ueber die Darstellung und Reactionen von Formamidin-derivaten", F.B. Dains.
J. Org. Chem. 61, (month unavailable) 1996, pp. 4125–4129, "Preparation and Stereochemistry Of Dioxatetraazaperhydroanthracenes and –perylenes from the Reaction of 2–Hydrazinoethanols with Aldehydes and Glutaraldehyde", Tadashi Okawara, Shuji Ehara, Hideaki Kagotani, Yoshinari Okamoto, Masashi Eto, Kazunobu Harano, Tetsuo Yamasaki and Mitsuru Furukawa.
J. Amer. Chem. Soc. 99, Feb. 16, 1977, pp. 1172–1179, "Olefins from Thermal Decomposition Of N–Sulfoximino–2–oxazolidones. A Novel Synthesis of Bicyclo[3.3.1]non–1–ene", Moon–geu Kim and James D. White.

(List continued on next page.)

Primary Examiner—Joseph K. McKane
Assistant Examiner—Golam M M Shameem
(74) Attorney, Agent, or Firm—Richard E. L. Henderson; Raymond J. Harmuth

(57) ABSTRACT

According to a novel process, microbicidally active 2-(1,2,4-triazol-1-yl)-ethanols of the formula

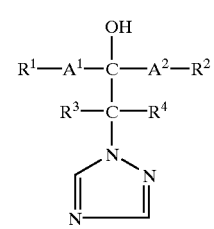

(I)

in which $A^1, A^2, R^1, R^2, R^3$ and $R^4$ are as defined in the description, can be prepared by reacting hydrazine derivatives of the formula

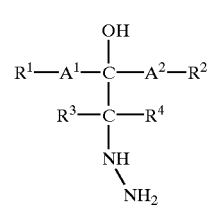

(II)

with N-dihalogenomethyl-formamidinium halide of the formula

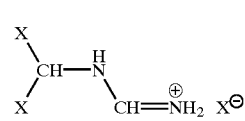

(III)

in which

X represents chlorine or bromine, if appropriate in the presence of a diluent.

7 Claims, No Drawings

OTHER PUBLICATIONS

Bull. Soc. Chim. Fr., (month unavailable) 1947, pp. 850–857, "Recherches en série alicyclique (19° mémoire). Etude des amino–alcools", Max Mousseron et Robert Granger .

Bull. Soc. Chim. Fr. (month unavailable) 1939, pp. 708–715, "Hydroxyalcoylhydrazines", M. G. Benoit.

*U. Bechstein et al: "Efficient syntheses of omega–chloro–, omega–imido– and omega–aminoalkyl–1,2, 4–triazoles from N–acyl–formamidinium salts or N–acylformamides and hydrazines" Archiv Der Pharmazie, Bd. 325, Nr. 8, 1992, Seiten 519–529, XP999887749 Weinheim des ganze Dokument.

* cited by examiner

METHOD FOR PRODUCING 2-(1,2,4-TRIAZOL-1-YL)-ETHANOLS

The present invention relates to a novel process for preparing 2-(1,2,4-triazol-1-yl)-ethanols having microbicidal, in particular fungicidal, properties.

It is already known that numerous 2-(1,2,4-triazol-1-yl)-ethanols can be prepared by reacting appropriately substituted oxiranes with 1,2,4-triazole in the presence of a base and a diluent. However, this process has the disadvantage that, in addition to the desired 1,2,4-triazol-1-yl compounds (="asymmetric triazole"), varying proportions of interfering 1,3,4-triazol-1-yl derivatives (="symmetric triazole") are also obtained (cf. Tetrahedron Lett. 30 (1989) 4013–4016). Naturally, this reduces the yield of the 1,2,4-triazol-1-yl derivative. Moreover, removal of the interfering 1,3,4-triazol-1-yl compound renders work-up more difficult, so that the yield of 1,2,4-triazol-1-yl derivative is frequently reduced even further.

It is also already known that 1,2,4-triazoles which are substituted in the 1-position can be obtained by reacting substituted hydrazines with [2-aza-3-(dimethylamino)-2-propene-1-ylidene]-dimethylimmonium chloride ("Gold's reagent") (cf. Angew. Chem. 72 (1960) 956–959). However, the yields are not satisfactory. A further disadvantage is the fact that 2 mol of dimethylamine are produced per mole of triazolyl derivative.

It is furthermore already known that 1,2,4-triazoles which are substituted in the 1-position can be obtained by reacting hydrazine derivatives with formamidine acetate (cf. "N—C—N Chemicals; Formamidine; Building block for heterocycles and intermediates", company publication from SKW Trostberg AG, 1989). Thus, 2-(1-chloro-cyclopropyl)-1-(2-chloro-phenyl)-3-(1,2,4-triazol-1-yl)-propane-2-ol can be synthesized by reacting 2-(1-chloro-cyclopropyl)-2-(2-chlorobenzyl)-oxirane with hydrazine hydrate, followed by reaction of the resulting 2-(1-chloro-cycloprop-1-yl)-3-(2-chlorophenyl)-2-hydroxy-propyl-hydrazine with formamidine acetate (cf. DE-A 40 30 039). However, it is disadvantageous that the yield of the desired target product is relatively low.

It has now been found that 2-(1,2,4-triazol-1-yl)-ethanols of the formula

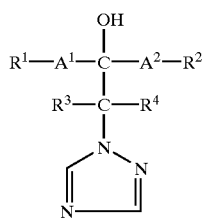
(I)

in which
- $A^1$ and $A^2$ independently of one another represent a direct bond, represent optionally halogen-substituted alkanediyl, represent optionally halogen-substituted alkenediyl, represented optionally halogen-substituted alkinediyl or represent alkanediyl in which a methylene group is replaced by oxygen,
- $R^1$ and $R^2$ independently of one another represent hydrogen, represent optionally substituted cycloalkyl or represent optionally substituted aryl and
- $R^3$ and $R^4$ independently of one another represent hydrogen or represent optionally substituted alkyl or

- $R^3$ and $R^4$ together with the carbon atom to which they are attached represent optionally substituted cycloalkyl, or
- $R^1$, $A^1$ and $R^3$ together with the carbon atoms to which they are attached represent cycloalkyl,
- $A^2$ represents a direct bond, represents optionally halogen-substituted alkanediyl, represents optionally halogen-substituted alkenediyl, represents optionally halogen-substituted alkinediyl or represents alkanediyl in which one methylene group has been replaced by oxygen,
- $R^2$ represents hydrogen, represents optionally substituted cycloalkyl or represents optionally substituted aryl and
- $R^4$ represents hydrogen or represents optionally substituted alkyl, or
- $R^3$ and $R^4$ represent hydrogen and the groups
- $R^1$—$A^1$— and $R^2$—$A^2$— together with the carbon atom to which they are attached represent a radical of the formula

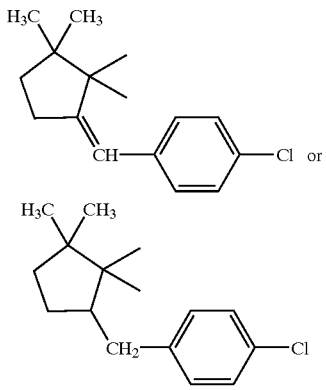

can be prepared by reacting hydrazine derivatives of the formula

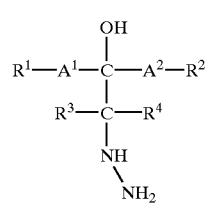
(II)

in which
$A^1$, $A^2$, $R^1$, $R^2$, $R^3$ and $R^4$ are as defined above
with N-dihalogenomethyl-formamidinium halide of the formula

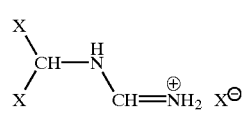
(III)

in which
X represents chlorine or bromine,
if appropriate in the presence of a diluent.

It is extremely surprising that 2-(1,2,4-triazol-1-yl)-ethanols of the formula (I) can be prepared by the process according to the invention in a smooth reaction, since the prior art indicated that there would be interfering sidereactions and decomposition of N-dihalogenomethyl-formamidinium halide of the formula (III). Thus, it follows from Ber. dtsch. Chem. Ges. 16 (1883) 308–311 that N-dichloromethyl-formamidinium chloride is decomposed by water or alcohols. Furthermore, Chem. Ber. 35, (1902) 2496–2511 describes that one equivalent of N-dichloromethylformamidinium chloride reacts easily and completely with two equivalents of a primary amine of the formula R—NH$_2$ with elimination of three equivalents of hydrogen chloride to give one equivalent of formamidine and one equivalent of disubstituted formamidine of the formula R—N=CH—NH—R. The reaction of o-phenylenediamine with N-dichloromethyl-formamidinium chloride gives benzimidazole (cf. Chem. Ber. 35 (1902), 2496–2511). Phenylhydrazine reacts with N-dichloromethylformamidinium chloride like primary amine; however, the formamidine derivative formed is oxidized further by atmospheric oxygen or a third equivalent of phenylhydrazine to give diphenylformazane of the formula Ph—N=N—CH=N—NH—Ph (cf. Chem. Ber. 35 (1902), 2496–2511). The formation of 1-phenyl-1,2,4-triazole from phenylhydrazine and N-dichloromethyl-formamidinium chloride has not been reported. Taking into account these known reactions, it was without any doubt contrary to expectations that the reaction according to the invention would give the desired type of products in high yield.

The process according to the invention has a number of advantages. Thus, as already mentioned, it makes possible the synthesis of 2-(1,2,4-triazol-1-yl)-ethanols of the formula (I) in high yield, free from the corresponding "symmetric" triazole derivatives. Moreover, it is favourable that the required starting materials and reaction components can be prepared in a simple manner and are available even in relatively large amounts. Finally, it is a further advantage that the yields are higher than those for comparable reactions of hydrazines with formamidine acetate or "Gold's reagent". Compared to the use of "Gold's reagent", it is furthermore favourable that the reactions according to the invention with N-dihalogenomethyl-formamidinium halide produce only hydrogen halide and ammonia.

Using [1-(2-chlorophenyl)-2-(1-chloro-cyclopropyl)-2-hydroxy]-propylhydrazine hydrochloride and N-dichloromethyl-formamidinium chloride as starting materials, the course of the process according to the invention can be illustrated by the formula scheme below.

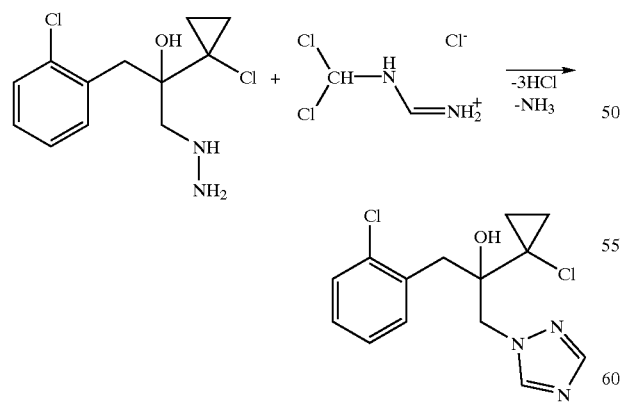

The formula (II) provides a general definition of the hydrazine derivatives required as starting materials for carrying out the process according to the invention. Preference is given to using hydrazine derivatives of the formula (II) in which A$^1$ represents a direct bond, represents optionally halogen-substituted, straight-chain or branched alkanediyl having 1 to 4 carbon atoms, represents optionally halogen-substituted, straight-chain or branched alkenediyl having 2 to 4 carbon atoms, represents optionally halogen-substituted straight-chain or branched alkinediyl having 2 to 4 carbon atoms or represents straight-chain or branched alkanediyl in which one methylene group has been replaced by oxygen, having 2 to 4 chain members, A$^2$ represents a direct bond, represents optionally halogen-substituted straight-chain or branched alkanediyl having 1 to 6 carbon atoms, represents optionally halogen-substituted straight-chain or branched alkenediyl having 2 to 6 carbon atoms or represents optionally halogen-substituted straight-chain or branched alkinediyl having 2 to 6 carbon atoms, R$^1$ represents cycloalkyl having 3 to 7 carbon atoms which is optionally mono- to trisubstituted by identical or different substituents from the group consisting of fluorine, chlorine, bromine and/or alkyl having 1 to 4 carbon atoms or represents aryl having 6 to 10 carbon atoms which may be mono- to trisubstituted by identical or different substituents from the group consisting of fluorine, chlorine, bromine, alkyl having 1 to 4 carbon atoms, cyano, nitro, alkoxy having 1 to 4 carbon atoms, alkylthio having 1 to 4 carbon atoms, halogenoalkyl having 1 to 4 carbon atoms and 1 to 9 fluorine, chlorine and/or bromine atoms, halogenoalkoxy having 1 to 4 carbon atoms and 1 to 9 fluorine, chlorine and/or bromine atoms or halogenoalkylthio having 1 to 4 carbon atoms and 1 to 9 fluorine, chlorine and/or bromine atoms, R$^2$ represents hydrogen or represents cycloalkyl having 3 to 7 carbon atoms which is optionally mono- to trisubstituted by identical or different substituents from the group consisting of fluorine, chlorine, bromine and alkyl having 1 to 4 carbon atoms or represents aryl having 6 to 10 carbon atoms which may be mono- to trisubstituted by identical or different substituents from the group consisting of fluorine, chlorine, bromine, alkyl having 1 to 4 carbon atoms, cyano, nitro, alkoxy having 1 to 4 carbon atoms, alkylthio having 1 to 4 carbon atoms, halogenoalkyl having 1 to 4 carbon atoms and 1 to 9 fluorine, chlorine and/or bromine atoms, halogenoalkoxy having 1 to 4 carbon atoms and 1 to 9 fluorine, chlorine and/or bromine atoms and halogenoalkylthio having 1 to 4 carbon atoms and 1 to 9 fluorine, chlorine and/or bromine atoms, and R$^3$ and R$^4$ independently of one another represent hydrogen or alkyl having 1 to 4 carbon atoms which is optionally mono- to trisubstituted by identical or different substituents from the group consisting of fluorine, chlorine, bromine and alkoxy having 1 or 2 carbon atoms or R$^3$ and R$^4$ together with the carbon atom to which they are attached represent cycloalkyl having 3 to 6 carbon atoms which is optionally mono- to trisubstituted by identical or different substituents from the group consisting of fluorine, chlorine, bromine and alkyl having 1 to 4 carbon atoms, or R$^1$, A$^1$ and R$^3$ together with the carbon atoms to which they are attached represent cycloalkyl having 3 to 6 carbon atoms, $A^2$ represents a direct bond, $R^2$ represents hydrogen or represents cycloalkyl having 3 to 7 carbon atoms which is optionally mono- to trisubstituted by identical or different substituents from the group consisting of fluorine, chlorine, bromine and alkyl having 1 to 4 carbon atoms or represents aryl having 6 to 10 carbon atoms which may be mono- to trisubstituted by identical or different substituents from the group consisting of fluorine, chlorine, bromine, alkyl having 1 to 4 carbon atoms, cyano, nitro, alkoxy having 1 to 4 carbon atoms, alkylthio having 1 to 4 carbon atoms, halogenoalkyl having 1 to 4 carbon atoms and 1 to 9 fluorine, chlorine and/or bromine atoms, halogenoalkoxy having 1 to 4 carbon atoms and 1 to 9 fluorine, chlorine and/or bromine atoms or halogenoalkylthio having 1 to 4 carbon atoms and 1 to 9 fluorine, chlorine and/or bromine atoms, and $R^4$ represents hydrogen or represents alkyl having 1 to 4 carbon atoms which is optionally mono- to trisubstituted by identical or different substituents from the group consisting of fluorine, chlorine, bromine and alkoxy having 1 or 2 carbon atoms, or $R^3$ and $R^4$ represent hydrogen and the groups $R^1$—$A^1$— and $R^2$—$A^2$— together with the carbon atoms to which they are attached represent a radical of the formula

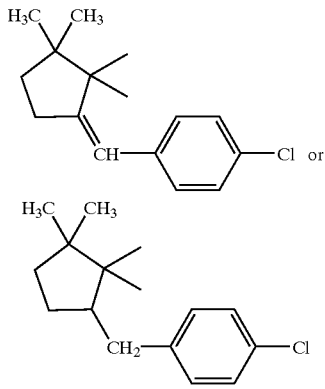

Particular preference is given to hydrazine derivatives of the formula (II) in which $A^1$ represents a single bond, represents methylene, ethane-1,1-diyl, ethane-1,2-diyl, ethene-1,2-diyl, ethine-1,2-diyl or —O—$CH_2$, where the $CH_2$ group is attached to the carbinol carbon atom, $A^2$ represents a direct bond or represents methylene, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, butane-2,2-diyl, 2-methyl-propane-1,2-diyl, ethylene-1,2-diyl or ethine-1,2-diyl, each of which is optionally mono- or disubstituted by fluorine and/or chlorine, $R^1$ represents cycloalkyl having 3 to 6 carbon atoms which is optionally mono- to trisubstituted by identical or different substituents from the group consisting of fluorine, chlorine, bromine, methyl, ethyl, n-propyl, i-propyl, n-butyl, iso-butyl, sec-butyl and tert-butyl or represents phenyl or naphthyl, each of which may be mono- to trisubstituted by identical or different substituents from the group consisting of fluorine, chlorine, bromine, cyano, nitro, methyl, ethyl, n-propyl, i-propyl, n-butyl, sec-butyl, iso-butyl, tert-butyl, methoxy, ethoxy, methylthio, ethylthio, trifluoromethyl, trifluoromethoxy, difluoromethoxy, trifluoromethylthio and difluoromethylthio, $R^2$ represents hydrogen or represents cycloalkyl having 3 to 6 carbon atoms which is optionally mono- to trisubstituted by identical or different substituents from the group consisting of fluorine, chlorine, bromine, methyl, ethyl, n-propyl, i-propyl, n-butyl, iso-butyl, sec-butyl and tert-butyl or represents phenyl or naphthyl, each of which may be mono- to trisubstituted by identical or different substituents from the group consisting of fluorine, chlorine, bromine, cyano, nitro, methyl, ethyl, n-propyl, i-propyl, n-butyl, sec-butyl, iso-butyl, tert-butyl, methoxy, ethoxy, methylthio, ethylthio, trifluoromethyl, trifluoromethoxy, difluoromethoxy, trifluoromethylthio and difluoromethylthio, $R^3$ and $R^4$ independently of one another represent hydrogen, methyl or ethyl or $R^3$ and $R^4$ together with the carbon atom to which they are attached represent cyclopropyl, cyclobutyl, cyclopentyl or cyclohexyl or $R^1$, $A^1$ and $R^3$ together with the carbon atoms to which they are attached represent cyclopropyl, cyclobutyl, cyclopentyl or cyclohexyl, $A^2$ represents a direct bond $R^2$ represents hydrogen or represents cycloalkyl having 3 to 6 carbon atoms which is optionally mono- to trisubstituted by identical or different substituents from the group consisting of fluorine, chlorine, bromine, methyl, ethyl, n-propyl, i-propyl, n-butyl, iso-butyl, sec-butyl and tert-butyl, or represents phenyl or naphthyl, each of which may be mono- to trisubstituted by identical or different substituents from the group consisting of fluorine, chlorine, bromine, cyano, nitro, methyl, ethyl, n-propyl, i-propyl, n-butyl, sec-butyl, iso-butyl, tert-butyl, methoxy, ethoxy, methylthio, ethylthio, trifluoromethyl, trifluoromethoxy, difluoromethoxy, trifluoromethylthio and difluoromethylthio and $R^4$ represents hydrogen, methyl or ethyl, or $R^3$ and $R^4$ represent hydrogen and the groups $R^1$—$A^1$— and $R^2$—$A^2$— together with the carbon atom to which they are attached represent a radical of the formula

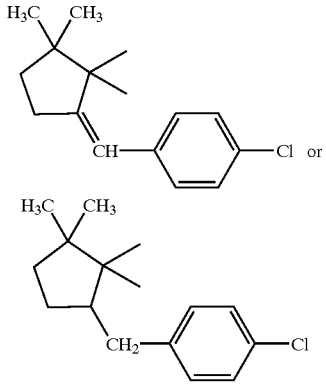

The hydrazine derivatives of the formula (II) are known or can be prepared by known methods. Thus, hydrazine derivatives of the formula (II) can be obtained by reacting oxiranes of the formula

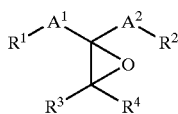

(IV)

in which
A$^1$, A$^2$, R$^1$, R$^2$, R$^3$ and R$^4$ are as defined above with hydrazine or hydrazine hydrate (cf. J. Org. Chem. 61 (1996) 4125; J. Amer. Chem. Soc. 99 (1977) 1172; Bull. Soc. Chim. Fr. 1947 850; and Bull. Soc. Chim. Fr. 1939, 708).

The oxiranes of the formula (IV) are known or can be prepared by known methods.

The hydrazine derivatives of the formula (II) can be employed either as free bases or in the form of their salts, such as, for example, their hydrochlorides, hydrobromides or hydrogen sulphates. Preference is given to using the hydrochlorides.

The formula (III) provides a general definition of the N-dihalogenomethyl-formamidinium halides furthermore required as starting materials for carrying out the process according to the invention. In this formula, X preferably represents chlorine.

The N-dihalogenomethyl-formamidinium halides (III) are known or can be prepared by known methods. Thus, N-dihalogenomethyl-formamidinium halides of the formula (III) are obtained by reacting 2 equivalents of hydrocyanic acid with 3 equivalents of hydrogen halide. The N-dihalogenomethyl-formamidinium halides are also referred to as sesquihydrohalides of hydrocyanic acid. N-Dichloromethyl-formamidinium chloride can be prepared, for example, by introducing dry hydrogen chloride into a solution, cooled to about −10° C., of hydrocyanic acid in a diluent, such as, for example, ethyl acetate (cf. Ber. dtsch. Chem. Ges. 16 (1883) 308–311). N-Dichloromethyl-formamidinium chloride can be represented by the formula

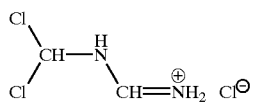

(III-1)

However, other structures are also possible (cf. Chem. Ber. 99 (1966), 431–444). For the sake of simplicity, only the formula (III-1) is used hereinafter, but this does not imply that a decision about the actual structure of the sesquihydrochloride of hydrocyanic acid has been made.

Suitable diluents for carrying out the process according to the invention are, in principle, all customary inert organic solvents. Preference is given to using carboxylic esters, such as methyl formate, ethyl formate, ethyl acetate and methyl acetate, furthermore ethers, such as tert-butyl methyl ether and 1,4-dioxane, furthermore N,N-disubstituted acid amides, such as N,N-dimethylformamide, N,N-dimethylacetamide and N-methylpyrrolidone, and additionally aromatic or aliphatic hydrocarbons, such as toluene, xylene, cyclohexane and methylcyclohexane. Particular preference is given to methyl acetate, ethyl acetate and toluene.

When carrying out the process according to the invention, the reaction temperatures can be varied within a relatively wide range. Frequently, the upper limit of the temperature range is given by the decomposition temperature of the hydrazine derivative of the formula (II). In general, the process is carried out at temperatures between 20 and 200° C., preferably between 30 and 150° C.

The process according to the invention is generally carried out under atmospheric pressure. However, it is also possible to operate under elevated or reduced pressure.

When carrying out the process according to the invention, the ratio in which the reaction components are employed can be varied within a relatively wide range. For economical reasons, at least 1 mol of N-dihalogenomethyl-formamidinium halide of the formula (III) is employed per mole of hydrazine derivative of the formula (II) or its salt. However, it is also possible to use less than 1 mol of N-dihalogenomethyl-formamidinium halide. Preferably, the N-dihalogenomethylformamidinium halide of the formula (III) is employed in an excess of from 1 to 30 mol %, particularly preferably from 5 to 20 mol %. Work-up is carried out by customary methods. In general, the reaction mixture is admixed with water and an organic solvent which is sparingly miscible with water, the organic phase is separated off, the aqueous phase is extracted with an organic solvent and the combined organic phases are dried and concentrated. Any impurities which may still be present can be removed by customary methods, for example by recrystallization, distillation or chromatographically.

The 2-(1,2,4-triazol-1-yl)-ethanols of the formula (I) preparable by the process according to the invention are known (cf. EP-A 0 040 345 and EP-A 0 297 345).

The 2-(1,2,4-triazol-1-yl)-ethanols of the formula (I) have microbicidal, in particular fungicidal, properties.

The practice of the process according to the invention is illustrated by the examples below.

PREPARATION EXAMPLES

Example 1

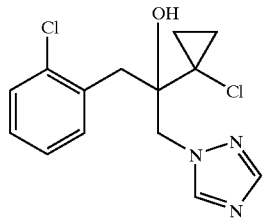

3.12 g of 2-(1-chloro-cycloprop-1-yl)-3-(2-chlorophenyl)-2-hydroxy-propyl-1-hydrazine hydrochloride, the content of which had been determined to be 95% (=9.5 mmol), are suspended at room temperature in 25 ml of ethyl acetate. 2 g (12 mmol) of N-dichloromethyl-formamidinium chloride are added, and the mixture is stirred at 45° C. for 5 hours. At room temperature, the reaction mixture is then admixed with 20 ml of water and 30 ml of ethyl acetate. The aqueous phase is separated off and extracted with 15 ml of ethyl acetate. The combined organic phases are dried over sodium sulphate and concentrated under reduced pressure. This gives 3.59 g of a product which comprises 82.3% (HPLC) of 2-(1-chloro-cyclopropyl)-1-(2-chlorophenyl)-3-(1,2,4-triazol-1-yl)-propan-2-ol. Accordingly, the calculated yield is 99.6% of theory.

Example 2

The procedure of Example 1 is repeated, but using only 1.72 g (10.5 mmol) of N-dichloromethyl-formamidinium chloride. This gives 3.43 g of a product which comprises 84.9% (HPLC) of 2-(1-chloro-cyclopropyl)-1-(2- chlorophenyl)-3-(1,2,4-triazol-1-yl)-propan-2-ol. Accordingly, the calculated yield is 98.2% of theory.

Example 3

10 mmol of 2-(1-chloro-cycloprop-1-yl)-3-(2-chlorophenyl)-2-hydroxy-propyl-1-hydrazine hydrochloride are suspended at room temperature in 25 ml of toluene. 1.72 g (10.5 mmol) of N-dichloromethyl-formamidinium chloride are added and the mixture is stirred under reflux for 5 hours. At room temperature, the reaction mixture is then admixed with 20 ml of water and 30 ml of toluene. The aqueous phase is separated off and extracted with 15 ml of toluene. The combined organic phases are dried over sodium sulphate and concentrated under reduced pressure. This gives 3.47 g of a product which comprises 89.9% (HPLC) of 2-(1-chloro-cyclopropyl)-1-(2-chlorophenyl)-3-(1,2,4-triazol-1-yl)-propan-2-ol. Accordingly, the calculated yield is 100% of theory.

Example 4

The procedure of Example 2 is repeated, but using, as solvent, ethyl formate instead of ethyl acetate.

The yield of 2-(1-chloro-cyclopropyl)-1-(2-chlorophenyl)-3-(1,2,4-triazol-1-yl)-propan-2-ol is 78% of theory.

Example 5

The procedure of Example 2 is repeated, but using, as solvent, N,N-dimethylformamide instead of ethyl acetate.

The yield of 2-(1-chloro-cyclopropyl)-1-(2-chlorophenyl)-3-(1,2,4-triazol-1-yl)-propan-2-ol is 63% of theory.

Example 6

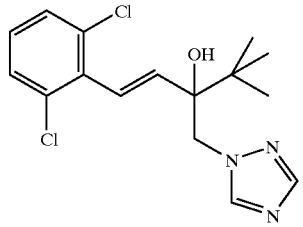

10 mmol of 2-tert-butyl-4-(2,6-dichlorophenyl)-2-hydroxy-but-3-en-1-hydrazine hydrochloride are suspended in 25 ml of ethyl acetate. 2 g (12 mmol) of N-dichloromethyl-formamidinium chloride are added and the mixture is stirred at 45° C. for 5 hours. At room temperature, the reaction mixture is stirred with 20 ml of water and 30 ml of ethyl acetate. The phases are separated and the aqueous phase is extracted again with 15 ml of ethyl acetate. The combined organic phases are dried over sodium sulphate and concentrated under reduced pressure. This gives 3.06 g of 3-tert-butyl-1-(2,6-dichlorophenyl)-4-(1,2,4-triazol-1-yl)-but-1-en-3-ol (90% of theory).

$^1$H-NMR (400 MHz, CDCl$_3$): δ=1.15 (s; 9H), 4.55–4.64 (m; 2H), 6.16 (d, J=16 Hz; 1H), 6.38 (d, J=16 Hz; 1H), 6.98 (m; 1H), 7.15 (m; 2H), 8.25 (s; 1H), 9.04 (s; 1H) ppm.

Example 7

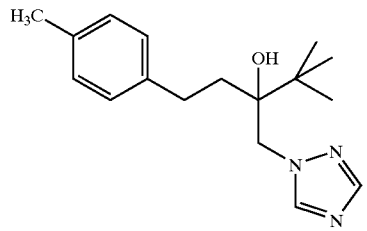

10 mmol of 2-tert-butyl-4-(4-methyl-phenyl)-2-hydroxy-butyl-1-hydrazine hydrochloride are suspended in 25 ml of ethyl acetate. 2 g (12 mmol) of N-dichloromethyl-formamidinium chloride are added and the mixture is stirred at 45° C. for 5 hours. At room temperature, the reaction mixture is stirred with 20 ml of water and 30 ml of ethyl acetate. The phases are separated and the aqueous phase is extracted again with 15 ml of ethyl acetate. The combined organic phases are dried over sodium sulphate and concentrated under reduced pressure. This gives 2.06 g of an oil which, according to HPLC, comprises 69% of 3-tert-butyl-1-(4-methylphenyl)-4-(1,2,4-triazol-1-yl)-butan-3-ol. Accordingly, the calculated yield is 49% of theory.

LC/MS (ESI positive): MH$^+$=288

Example 8

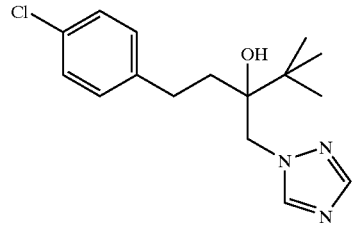

10 mmol of 2-tert-butyl-4-(4-chloro-phenyl)-2-hydroxy-butyl-1-hydrazine hydrochloride are suspended in 25 ml of ethyl acetate. 2 g (12 mmol) of N-dichloromethyl-formamidinium chloride are added and the mixture is stirred at 45° C. for 5 hours. At room temperature, the reaction mixture is stirred with 20 ml of water and 30 ml of ethyl acetate. The phases are separated and the aqueous phase is extracted again with 15 ml of ethyl acetate. The combined organic phases are dried over sodium sulphate and concentrated under reduced pressure. This gives 3.1 g of a solid which, according to HPLC, comprises 96.7% of 3-tert-butyl-1-(4-chloro-phenyl)-4-(1,2,4-triazol-1-yl)-butan-3-ol. Accordingly, the calculated yield is 97% of theory.

$^1$H-NMR (400 MHz, d-DMSO): δ=0.93 (s; 9H), 1.60–1.64 (m; 1H), 1.73–1.78 (m; 1H), 1.95–1.99 (m; 1H), 2.53–2.56 (m; 1H), 4.30–4.43 (m; 2H), 7.14 (m, 2H), 7.29 (m; 2H), 8.20 (s; 1H), 8.76 (s; 1H) ppm.

Example 9

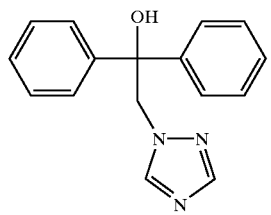

10 mmol of 2,2-diphenyl-2-hydroxy-ethyl-1-hydrazine hydrochloride are suspended in 25 ml of ethyl acetate. 2 g (12 mmol) of N-dichloromethyl-formamidinium chloride are added and the mixture is stirred at 45° C. for 5 hours. At room temperature, the reaction mixture is stirred with 20 ml of water and 15 ml of ethyl acetate. The solid is filtered off, washed with water and ethyl acetate and dried. This gives 2.0 g of a solid which, according to HPLC, comprises >99% of 1,1-diphenyl-2-(1,2,4-triazol-1-yl)-ethan-1-ol. Accordingly, the calculated yield is 66% of theory.

M.p.: 202–203° C.

The combined organic phases give, after drying over sodium sulphate and concentration under reduced pressure, a further 0.92 g of product which, according to HPLC, is 67% pure (=0.62 g=23% of theory).

$^1$H-NMR (400 MHz, CDCl$_3$): δ=4.90 (s; 2H), 7.25–7.28 (m; 2H), 7.30–7.33 (m; 4H), 7.40–7.42 (m; 4H), 7.69 (s; 1H), 7.83 (s; 1H) ppm.

Example 10

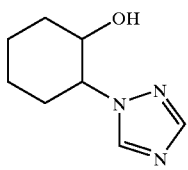

10 mmol of 2-hydroxy-cyclohex-1-yl-hydrazine are dissolved in 25 ml of ethyl acetate. 2 g (12 mmol) of N-dichloromethyl-formamidinium chloride are added and the mixture is stirred at 45° C. for 5 hours. At room temperature, the reaction mixture is stirred with 20 ml of water and 30 ml of ethyl acetate. The aqueous phase is separated off, neutralized with saturated aqueous sodium bicarbonate solution and extracted three times with in each case 30 ml of ethyl acetate. The organic phase is dried over sodium sulphate and concentrated under reduced pressure. This gives 0.48 g of a yellowish solid which, according to HPLC, comprises 92% of 2-(1,2,4-triazol-1-yl)-cyclohexanol. Accordingly, the calculated yield is 26% of theory.

Comparative Example
Preparation known from DE-A 40 30 039

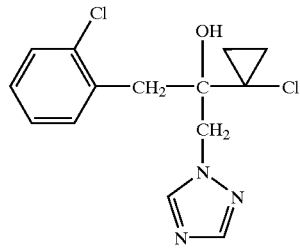

At temperatures between 65 and 70° C., 121.5 g (0.5 mol) of 2-(1-chloro-cyclopropyl)-2-(2-chloro-benzyl)-oxirane are added dropwise with stirring over a period of 2 hours to a mixture of 50 g (1 mol) of hydrazine hydrate and 200 ml of n-butanol. After the addition has ended, the mixture is stirred at 65 to 70° C. for a further 2 hours and then cooled to 20° C. The aqueous phase is separated off, the organic phase that remains is stirred with 50 ml of water, the organic phase is separated off and this organic phase is concentrated at 70° C. under reduced pressure.

The residue that remains is admixed with 200 ml of ethanol. At from 70 to 75° C., 114 g (1.1 mol) of formamidine acetate are added a little at a time with stirring to the resulting solution. After the addition has ended, the reaction mixture is heated with stirring at temperatures between 75 and 80° C. for another 10 hours. The reaction mixture is then worked up by concentration under reduced pressure at 70° C. The residue that remains at 70° C. is taken up in 350 ml of methylcyclohexane and, after addition of 200 ml of 45% strength by weight of aqueous sodium hydroxide solution, the pH is adjusted to a value between 7.5 and 8.0. The aqueous phase is separated off and the organic phase is, at 70° C., washed twice with in each case 200 ml of water. The organic phase is then separated off and slowly cooled to 20° C. The solid that precipitates is filtered off with suction washed twice with in each case 100 ml of methylcyclohexane and dried. This gives 117.5 g of a product which comprises 85% of 2-(1-chloro-cyclopropyl)-1-(2-chloro-phenyl)-3-(1,2,4-triazol-1-yl)-propan-2-ol.

Accordingly, the calculated yield is 64% of theory.

What is claimed is:

1. A process for preparing a 2-(1,2,4-triazol-1-yl)-ethanol of the formula (I)

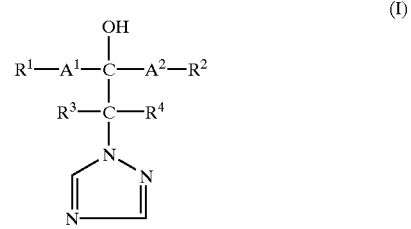

(I)

wherein
  A$^1$ and A$^2$ independently of one another represent a direct bond, represent optionally halogen-substituted alkanediyl, represent optionally halogen-substituted alkenediyl, represented optionally halogen-substituted alkinediyl or represent alkanediyl in which a methylene group is replaced by oxygen,
  R$^1$ and R$^2$ independently of one another represent hydrogen, represent optionally substituted cycloalkyl or represent optionally substituted aryl and $R^3$ and $R^4$ independently of one another represent hydrogen or represent optionally substituted alkyl or $R^3$ and $R^4$ together with the carbon atom to which they are attached represent optionally substituted cycloalkyl, or $R^1$, $A^1$ and $R^3$ together with the carbon atoms to which they are attached represent cycloalkyl, $A^2$ represents a direct bond, represents optionally halogen-substituted alkanediyl, represents optionally halogen-substituted alkenediyl, represents optionally halogen-substituted alkinediyl or represents alkanediyl in which one methylene group has been replaced by oxygen, $R^2$ represents hydrogen, represents optionally substituted cycloalkyl or represents optionally substituted aryl and $R^4$ represents hydrogen or represents optionally substituted alkyl, or $R^3$ and $R^4$ represent hydrogen and the groups $R^1$—$A^1$— and $R^2$—$A^2$— together with the carbon atom to which they are attached represent a radical of the formula

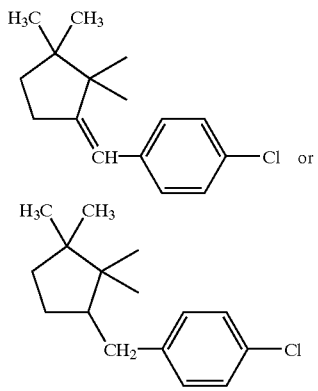

said process comprising the step of reacting a hydrazine derivative of the formula (II)

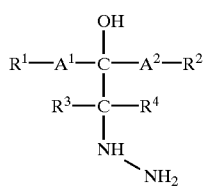

wherein $A^1$, $A^2$, $R^1$, $R^2$, $R^3$ and $R^4$ are as defined above with an N-dihalogenomethyl-formamidinium halide of the formula (III)

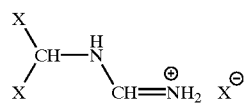

wherein

X represents chlorine or bromine, optionally in the presence of a diluent.

2. The process according to claim 1, wherein in said hydrazine derivative of the formula (II)

$A^1$ represents a direct bond, represents optionally halogen-substituted, straight-chain or branched alkanediyl having 1 to 4 carbon atoms, represents optionally halogen-substituted, straight-chain or branched alkenediyl having 2 to 4 carbon atoms, represents optionally halogen-substituted straight-chain or branched alkinediyl having 2 to 4 carbon atoms or represents straight-chain or branched alkanediyl in which one methylene group has been replaced by oxygen, having 2 to 4 chain members, $A^2$ represents a direct bond, represents optionally halogen-substituted straight-chain or branched alkanediyl having 1 to 6 carbon atoms represents optionally halogen-substituted straight-chain or branched alkenediyl having 2 to 6 carbon atoms or represents optionally halogen-substituted straight-chain or branched alkinediyl having 2 to 6 carbon atoms, $R^1$ represents cycloalkyl having 3 to 7 carbon atoms which is optionally mono- to trisubstituted by identical or different substituents from the group consisting of fluorine, chlorine, bromine and/or alkyl having 1 to 4 carbon atoms or represents aryl having 6 to 10 carbon atoms which may be mono- to trisubstituted by identical or different substituents from the group consisting of fluorine, chlorine, bromine, alkyl having 1 to 4 carbon atoms, cyano, nitro, alkoxy having 1 to 4 carbon atoms, alkylthio having 1 to 4 carbon atoms, halogenoalkyl having 1 to 4 carbon atoms and 1 to 9 fluorine, chlorine and/or bromine atoms, halogenoalkoxy having 1 to 4 carbon atoms and 1 to 9 fluorine, chlorine and/or bromine atoms or halogenoalkylthio having 1 to 4 carbon atoms and 1 to 9 fluorine, chlorine and/or bromine atoms, $R^2$ represents hydrogen or represents cycloalkyl having 3 to 7 carbon atoms which is optionally mono- to trisubstituted by identical or different substituents from the group consisting of fluorine, chlorine, bromine and alkyl having 1 to 4 carbon atoms or represents aryl having 6 to 10 carbon atoms which may be mono- to trisubstituted by identical or different substituents from the group consisting of fluorine, chlorine, bromine, alkyl having 1 to 4 carbon atoms, cyano, nitro, alkoxy having 1 to 4 carbon atoms, alkylthio having 1 to 4 carbon atoms, halogenoalkyl having 1 to 4 carbon atoms and 1 to 9 fluorine, chlorine and/or bromine atoms, halogenoalkoxy having 1 to 4 carbon atoms and 1 to 9 fluorine, chlorine and/or bromine atoms and halogenoalkylthio having 1 to 4 carbon atoms and 1 to 9 fluorine, chlorine and/or bromine atoms, and $R^3$ and $R^4$ independently of one another represent hydrogen or alkyl having 1 to 4 carbon atoms which is optionally mono- to trisubstituted by identical or different substituents from the group consisting of fluorine, chlorine, bromine and alkoxy having 1 or 2 carbon atoms or $R^3$ and $R^4$ together with the carbon atom to which they are attached represent cycloalkyl having 3 to 6 carbon atoms which is optionally mono- to trisubstituted by identical or different substituents from the group consisting of fluorine, chlorine, bromine and alkyl having 1 to 4 carbon atoms, or $R^1$, $A^1$ and $R^3$ together with the carbon atoms to which they are attached represent cycloalkyl having 3 to 6 carbon atoms, $A^2$ represents a direct bond, $R^2$ represents hydrogen or represents cycloalkyl having 3 to 7 carbon atoms which is optionally mono- to trisubstituted by identical or different substituents from the group consisting of fluorine, chlorine, bromine and alkyl having 1 to 4 carbon atoms or represents aryl having 6 to 10 carbon atoms which may be mono- to trisubstituted by identical or different substituents from the group consisting of fluorine, chlorine, bromine, alkyl having 1 to 4 carbon atoms, cyano, nitro, alkoxy having 1 to 4 carbon atoms, alkylthio having 1 to 4 carbon atoms, halogenoalkyl having 1 to 4 carbon atoms and 1 to 9 fluorine, chlorine and/or bromine atoms, halogenoalkoxy having 1 to 4 carbon atoms and 1 to 9 fluorine, chlorine and/or bromine atoms or halogenoalkylthio having 1 to 4 carbon atoms and 1 to 9 fluorine, chlorine and/or bromine atoms, and $R^4$ represents hydrogen or represents alkyl having 1 to 4 carbon atoms which is optionally mono- to trisubstituted by identical or different substituents from the group consisting of fluorine, chlorine, bromine and alkoxy having 1 or 2 carbon atoms, or $R^3$ and $R^4$ represent hydrogen and the groups $R^1$—$A^1$— and $R^2$—$A^2$— together with the carbon atoms to which they are attached represent a radical of the formula

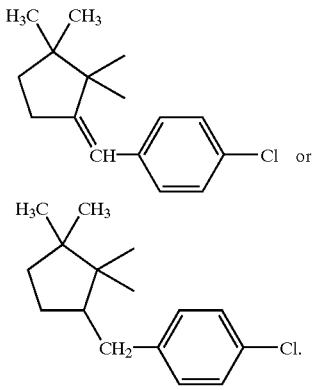

3. The process according to claim 1, wherein in said hydrazine derivative of the formula (II)

$A^1$ represents a single bond, represents methylene, ethane-1,1-diyl, ethane-1,2-diyl, ethene-1,2-diyl, ethine-1,2-diyl or —O—$CH_2$, where the $CH_2$ group is attached to the carbinol carbon atom, $A^2$ represents a direct bond or represents methylene, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, butane-2,2-diyl, 2-methyl-propane-1,2-diyl, ethylene-1,2-diyl or ethine-1,2-diyl, each of which is optionally mono- or disubstituted by fluorine and/or chlorine, $R^1$ represents cycloalkyl having 3 to 6 carbon atoms which is optionally mono- to trisubstituted by identical or different substituents from the group consisting of fluorine, chlorine, bromine, methyl, ethyl, n-propyl, i-propyl, n-butyl, iso-butyl, sec-butyl and tert-butyl or represents phenyl or naphthyl, each of which may be mono- to trisubstituted by identical or different substituents from the group consisting of fluorine, chlorine, bromine, cyano, nitro, methyl, ethyl, n-propyl, i-propyl, n-butyl, sec-butyl, iso-butyl, tert-butyl, methoxy, ethoxy, methylthio, ethylthio, trifluoromethyl, trifluoromethoxy, difluoromethoxy, trifluoromethylthio and difluoromethylthio, $R^2$ represents hydrogen or represents cycloalkyl having 3 to 6 carbon atoms which is optionally mono- to trisubstituted by identical or different substituents from the group consisting of fluorine, chlorine, bromine, methyl, ethyl, n-propyl, i-propyl, n-butyl, iso-butyl, sec-butyl and tert-butyl or represents phenyl or naphthyl, each of which may be mono- to trisubstituted by identical or different substituents from the group consisting of fluorine, chlorine, bromine, cyano, nitro, methyl, ethyl, n-propyl, i-propyl, n-butyl, sec-butyl, iso-butyl, tert-butyl, methoxy, ethoxy, methylthio, ethylthio, trifluoromethyl, trifluoromethoxy, difluoromethoxy, trifluoromethylthio and difluoromethylthio, $R^3$ and $R^4$ independently of one another represent hydrogen, methyl or ethyl or $R^3$ and $R^4$ together with the carbon atom to which they are attached represent cyclopropyl, cyclobutyl, cyclopentyl or cyclohexyl or $R^1$, $A^1$ and $R^3$ together with the carbon atoms to which they are attached represent cyclopropyl, cyclobutyl, cyclopentyl or cyclohexyl, $A^2$ represents a direct bond $R^2$ represents hydrogen or represents cycloalkyl having 3 to 6 carbon atoms which is optionally mono- to trisubstituted by identical or different substituents from the group consisting of fluorine, chlorine, bromine, methyl, ethyl, n-propyl, i-propyl, n-butyl, iso-butyl, sec-butyl and tert-butyl, or represents phenyl or naphthyl, each of which may be mono- to trisubstituted by identical or different substituents from the group consisting of fluorine, chlorine, bromine, cyano, nitro, methyl, ethyl, n-propyl, i-propyl, n-butyl, sec-butyl, iso-butyl, tert-butyl, methoxy, ethoxy, methylthio, ethylthio, trifluoromethyl, trifluoromethoxy, difluoromethoxy, trifluoromethylthio and difluoromethylthio and $R^4$ represents hydrogen, methyl or ethyl, or $R^3$ and $R^4$ represent hydrogen and the groups $R^1$—$A^1$— and $R^2$—$A^2$— together with the carbon atom to which they are attached represent a radical of the formula

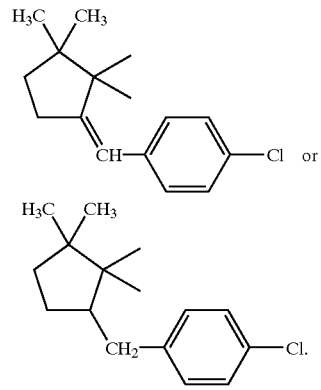

4. The process according to claim 1, wherein said hydrazine derivative of the formula (II) is employed in the form of an acid addition salt.

5. The process according to claim 1, wherein a reaction component of the N-dihalogenomethyl-formamidinium halide of the formula (III) is N-dichloromethyl-formamidinium hydrochloride.

6. The process according to claim 1, wherein said process is carried out at temperatures between 20° C. and 200° C.

7. A process for preparing 2-(1-chloro-cyclopropyl)-1-(2-chlorophenyl)-3-(1,2,4-triazol-1-yl)-propan-2-ol comprising:

reacting 2-(1-chloro-cycloprop-1-yl)-3-(2-chlorophenyl)-2-hydroxy-propyl-1-hydrazine hydrochloride with N-dichloromethyl-formamidinium chloride.

* * * * *